(12) United States Patent
Im et al.

(10) Patent No.: US 12,064,750 B2
(45) Date of Patent: Aug. 20, 2024

(54) COBALT-BASED SINGLE-ATOM DEHYDROGENATION CATALYSTS HAVING HIGH SELECTIVITY AND REGENERABILITY AND METHOD FOR PRODUCING CORRESPONDING OLEFINS FROM PARAFFINS USING THE SAME

(71) Applicant: SK Innovation Co., Ltd., Seoul (KR)

(72) Inventors: Ju Hwan Im, Daejeon (KR); Dong Min Yun, Daejeon (KR); Ho Won Lee, Daejeon (KR); Young Eun Cheon, Daejeon (KR); Hee Soo Kim, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 17/472,850

(22) Filed: Sep. 13, 2021

(65) Prior Publication Data
US 2022/0105496 A1   Apr. 7, 2022

(30) Foreign Application Priority Data

Sep. 17, 2020 (KR) ........................ 10-2020-0119634
Nov. 18, 2020 (KR) ........................ 10-2020-0154365

(51) Int. Cl.
*B01J 21/06* (2006.01)
*B01J 23/75* (2006.01)
(Continued)

(52) U.S. Cl.
CPC ............. *B01J 23/75* (2013.01); *B01J 21/066* (2013.01); *B01J 35/613* (2024.01); *B01J 35/615* (2024.01);
(Continued)

(58) Field of Classification Search
CPC ...... B01J 21/066; B01J 23/75; B01J 37/0213; B01J 37/08; B01J 35/1014; B01J 35/1019;
(Continued)

(56) References Cited

U.S. PATENT DOCUMENTS 4,639,430 A   1/1987  Pasquet et al.
5,347,046 A   9/1994  White et al.
(Continued)

FOREIGN PATENT DOCUMENTS

CN   86103269 A   12/1986
CN    1123527 A    5/1996
(Continued)

OTHER PUBLICATIONS

Schweitzer et al., "Propylene Hydrogenation and Propane Dehydrogenation by a Single-Site Zn2+ on Silica Catalyst", ACS Catalysis, 2014, pp. 1091-1098, vol. 4.
(Continued)

*Primary Examiner* — Jun Li
(74) *Attorney, Agent, or Firm* — The Webb Law Firm

(57) ABSTRACT

Provided is a dehydrogenation catalyst having single-atom cobalt loaded onto a support including a zirconia core surface-modified with silica, a method for producing the dehydrogenation catalyst, and a method for producing corresponding olefin through dehydrogenation of paraffin, particularly light paraffin, in the presence of the dehydrogenation catalyst.

12 Claims, 5 Drawing Sheets

(51) Int. Cl.
  *B01J 35/10* (2006.01)
  *B01J 35/61* (2024.01)
  *B01J 35/63* (2024.01)
  *B01J 37/02* (2006.01)
  *B01J 37/08* (2006.01)

(52) U.S. Cl.
  CPC ............ *B01J 35/633* (2024.01); *B01J 35/635* (2024.01); *B01J 37/0213* (2013.01); *B01J 37/08* (2013.01)

(58) Field of Classification Search
  CPC ............... B01J 35/1038; B01J 35/1042; C07C 2521/06
  See application file for complete search history.

(56) References Cited

U.S. PATENT DOCUMENTS

| | | | |
|---|---|---|---|
| 5,453,558 A | 9/1995 | Alexander et al. | |
| 5,475,144 A | 12/1995 | Watson et al. | |
| 6,103,103 A | 8/2000 | Alexander et al. | |
| 6,733,657 B2 | 5/2004 | Benazzi et al. | |
| 8,680,357 B1 | 3/2014 | Rokicki et al. | |
| 10,040,054 B2 | 8/2018 | Rytter et al. | |
| 2010/0185010 A1* | 7/2010 | Hagemeyer | C07C 67/055 502/227 |
| 2012/0016171 A1* | 1/2012 | Kustov | B01J 37/04 502/215 |
| 2013/0253248 A1 | 9/2013 | Gamoras et al. | |
| 2014/0128563 A1* | 5/2014 | McDaniel | C08F 210/14 526/348.5 |
| 2014/0274672 A1* | 9/2014 | Kauffman | B01J 27/1853 502/213 |
| 2014/0275686 A1* | 9/2014 | Hock | B01J 35/1019 502/259 |
| 2015/0141593 A1* | 5/2015 | Yang | C08F 4/65904 526/348.5 |
| 2016/0074838 A1 | 3/2016 | Hock et al. | |
| 2016/0199814 A1 | 7/2016 | Bai et al. | |
| 2018/0229220 A1* | 8/2018 | Dang | B01J 23/626 |
| 2021/0170370 A1 | 6/2021 | Lee et al. | |

FOREIGN PATENT DOCUMENTS

| | | |
|---|---|---|
| CN | 1151722 A | 6/1997 |
| CN | 1151723 A | 6/1997 |
| CN | 101108362 A | 1/2008 |
| CN | 104525183 A | 4/2015 |
| CN | 111252772 A | 6/2020 |
| EP | 3928864 A1 | 12/2021 |
| JP | 200829949 A | 2/2008 |
| JP | 2013505996 A | 2/2013 |
| JP | 2013511383 A | 4/2013 |
| KR | 100837195 B1 | 6/2008 |
| KR | 1020090116054 A | 11/2009 |
| KR | 1020180041794 A | 4/2018 |
| KR | 1020200049209 A | 5/2020 |
| KR | 1020210018566 A | 2/2021 |
| WO | 9633015 A1 | 10/1996 |
| WO | 2009136711 A2 | 11/2009 |

OTHER PUBLICATIONS

Silica—Silicon Dioxide (SiO2). Properties [online]. AZO Materials, 2001 [retrieved on Dec. 10, 2021]. Retrieved from the Internet: <URL: https://www.azom.com/properties.aspx?ArticleID=1114>.

Zirconia—ZrO2, Zirconium Dioxide. Properties [online]. AZO Materials, 2001 [retrieved on Dec. 10, 2021]. Retrieved from the Internet: <URL: https://www.azom.com/properties.aspx?ArticleID=133>.

Keyvanloo et al., "Supported Iron Fischer-Tropsch Catalyst: Superior Activity and Stability Using a Thermally Stable Silica-Doped Alumina Support", American Chemical Society, 2014, pp. 1071-1077, vol. 4.

Zhao et al., "Zirconium Modification Promotes Catalytic Activity of a Single-Site Cobalt Heterogeneous Catalyst for Propane Dehydrogenation" American Chemical Society, 2018, pp. 11117-11127, vol. 3.

Goldsmith et al., "Beyond Ordered Materials: Understanding Catalytic Sites on Amorphous Solids", ACS Catal., 2017, pp. 7543-7557, vol. 7.

Jimenez et al., "Influence of coordination environment of anchored single-site cobalt catalyst on CO2 hydrogenation", ChemCatChem, 2019, pp. 1-10.

* cited by examiner

COBALT-BASED SINGLE-ATOM DEHYDROGENATION CATALYSTS HAVING HIGH SELECTIVITY AND REGENERABILITY AND METHOD FOR PRODUCING CORRESPONDING OLEFINS FROM PARAFFINS USING THE SAME

CROSS-REFERENCE TO RELATED APPLICATIONS

This application claims priority to Korean Patent Application Nos. 10-2020-0119634 filed Sep. 17, 2020 and 10-2020-0154365 filed Nov. 18, 2020, the disclosures of which are hereby incorporated by reference in their entirety.

BACKGROUND OF THE INVENTION

Field of the Invention

The present disclosure relates to a single-atom cobalt-based dehydrogenation catalyst having high selectivity and regenerability and a method for producing olefins from corresponding paraffins using the same. More particularly, the present disclosure relates to a dehydrogenation catalyst having single-atom cobalt loaded onto a support comprising a zirconia core surface-modified with silica, a method for producing corresponding olefins through dehydrogenation of paraffins, particularly light paraffins, in the presence of the dehydrogenation catalyst.

DESCRIPTION OF THE RELATED ART

Recently, attention has been paid to catalyst techniques of loading active metals onto supports and utilizing the same. Particularly, with the advance of nanotechnology, active studies on loading of nano-sized active metals onto supports are ongoing. Despite having excellent activity compared to conventional catalysts, nano-sized active metals, when used as catalysts, suffer from disadvantages of causing side reactions or undergoing rapid deactivation due to their broad size distribution and irregular morphologies.

Meanwhile, a catalyst having metal loaded in a single atomic size can maximize catalytic activity by reducing the size of active metal sites to a sub-nano-size atomic level. Specifically, due to the extremely simple and ideal structures thereof, single-atom catalysts are advantageous in simulating theoretical results obtained through computational science, etc. In this regard, catalysts, in which transition metals such as zinc (Zn) and cobalt (Co) are loaded in the form of single atom on supports (e.g., silica), have been used for dehydrogenation of light paraffins. In addition, it has been reported that, when supported, single-atom active metals convey the advantages of minimizing cracking and suppressing the formation of coke during catalytic reactions (e.g., ACS Catal. 2014, 4, 4, 1091-1098).

However, the prior art techniques have shortcomings from a commercial viewpoint because a mixed gas (containing 3% of propane and the balance of the inert gas argon (Ar) as reactants) is used to maintain a low concentration of reactants in selectively converting paraffins to the corresponding olefins while suppressing the formation of byproducts, and reactions should be performed at low temperatures in order to prolong the catalyst life spans. Moreover, when dehydrogenation of the paraffins in the presence of a catalyst having single-atom cobalt as an active metal loaded on a support is conducted at high temperatures, the aggregation (or agglomeration) of the cobalt elements immobilized on the support or the formation of elemental cobalt attributed to a reduction phenomenon occurs, thus making it difficult to secure long-term reaction stability or regenerability.

A variety of methods aiming to overcome the problems described above have been researched and reported (for example, Korean Patent Publication No. 2020-0049209 A). However, continuous exposure to high temperatures during the dehydrogenation decreases yield due to a decrease in the strength or durability of silica as a support after the reaction is repeated.

Therefore, there is a need for a single-atom catalyst that has excellent long-term reaction stability or regenerability compared to the prior art.

SUMMARY OF THE INVENTION

An embodiment according to the present disclosure provides a single-atom cobalt (Co)-loaded catalyst that is capable of improving long-term reaction stability or regenerability of a dehydrogenation catalyst used in the reaction for producing olefins from paraffins, and a preparation method therefor.

Provided according to a first aspect of the present disclosure is a method for producing a single-atom cobalt-based catalyst, which comprises:

a) surface-modifying a surface or outer portion of zirconia with silica to prepare a silica-modified zirconia support, b) preparing an aqueous dispersion of the silica-modified zirconia support, c) preparing a pH-adjusted aqueous dispersion of the silica-modified zirconia support by adding a base to the aqueous dispersion of the silica-modified zirconia support to adjust a pH of the aqueous dispersion to at least 10, d) separately, preparing a pH-adjusted aqueous cobalt precursor solution by preparing an aqueous solution of a cobalt precursor having an oxidation number of 3+ and adding a base to the aqueous solution, e) combining the pH-adjusted aqueous dispersion of the silica-modified zirconia support with the pH-adjusted aqueous solution of the cobalt precursor to prepare an aqueous dispersion in which at least a part of the cobalt ions having an oxidation number of 3+ is adsorbed onto a surface of the silica-modified zirconia support, f) removing cobalt ions which remain not adsorbed onto the silica-modified zirconia support, and g) thermally treating the cobalt ion-adsorbed silica-modified zirconia support obtained in step f), wherein the cobalt having an oxidation number of 2+ exists in an isolated form of single-atom on the silica-modified zirconia support while being tetrahedrally coordinated at a three-membered hydroxyl ring on the surface of the silica-modified zirconia support.

Provided according to a second aspect of the present disclosure is a single-atom cobalt-based dehydrogenation catalyst, which comprises:

a silica-modified zirconia support, in which zirconia, as a core, has been surface-modified with silica, and cobalt loaded as an active metal on the silica-modified zirconia support, wherein the cobalt having an oxidation number of 2+ exists in an isolated form of single-atom on the silica-modified zirconia support while being tetrahedrally coordinated at a three-membered hydroxyl ring on the surface of the silica-modified zirconia support.

Provided according to a third aspect of the present disclosure is a method for producing olefins from paraffins, which comprises:

providing a feedstock containing light paraffins, subjecting the feedstock to dehydrogenation at a temperature of 500 to 700° C. under a pressure of 0.3 to 2 bar in the presence of the catalyst described above, and recovering olefins corresponding to the light paraffin from the dehydrogenation product.

In the dehydrogenation catalyst according to an embodiment according to the present disclosure, a single-atom cobalt is loaded on a support comprising zirconia ($ZrO_2$), as a core, surface-modified with silica ($SiO_2$), thereby improving long-term reaction stability or regeneration stability during dehydrogenation of paraffin (particularly, light paraffin) attributed to the excellent strength or durability originating from zirconia, as well as the change of electronic properties of cobalt active sites. In addition, the surface or the outer portion of the zirconia core can be modified to be suitable for depositing cobalt in the form of single atom thereon even with a small amount of silica during the preparation of the support. In particular, the surface-modification can be performed using inexpensive silica precursor.

Furthermore, the catalyst according to an embodiment of the present disclosure is advantageous for commercialization because it can exhibit excellent conversion and olefin selectivity even for a feedstock containing a high paraffin content in the dehydrogenation.

BRIEF DESCRIPTION OF THE DRAWINGS

The above and other objects, features, and other advantages of the present disclosure will be more clearly understood from the following detailed description taken in conjunction with the accompanying drawings, in which.

DESCRIPTION OF THE INVENTION

Figure 1:
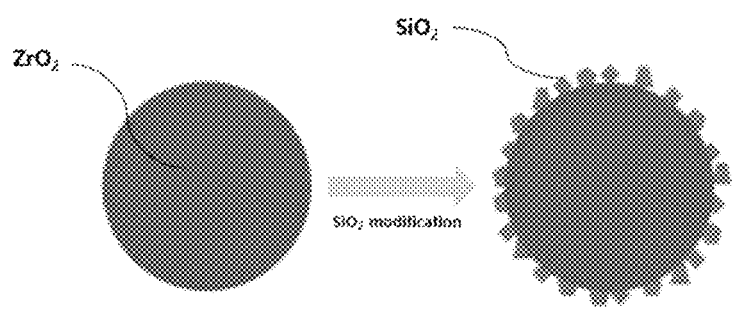
FIG. 1 is a schematic diagram illustrating an exemplary structure of the support, in which a surface or an outer portion of a zirconia core is surface-modified, according to an exemplary embodiment.

The present disclosure can be worked in its entirety with reference to the following description. It is to be understood that the following description illustrates preferable embodiments of the present disclosure, but the present disclosure is not necessarily limited thereto. It is also to be understood that the accompanying drawings are included to provide a further understanding of the present disclosure, and are not intended to limit the scope of the present disclosure.

The terms used herein are defined as follows.

As used herein, the term "heterogeneous catalyst" refers to a catalyst that is present in a different phase from a reactant in a catalytic reaction process. By way of example, a heterogeneous catalyst may remain undissolved in a reaction medium. When a heterogeneous catalyst is used, the onset of a reaction occurs with the diffusion and adsorption of reactants onto the surface of the heterogeneous catalyst. After completion of the reaction, a product needs to be desorbed from the surface of the heterogeneous catalyst.

As used herein, the term "support" refers to a material (typically a solid-phase material) having a large specific surface area, onto which a catalytically active component is attached or deposited, and the support may or may not be involved in a catalytic reaction.

As used herein, the term "zirconia" may include various stoichiometric forms of zirconium oxide, and more typically refers to zirconium oxide having the stoichiometric formula of $ZrO_2$.

As used herein, the term "silica" refers to a substance having tetrahedral coordination in which four oxygen atoms bind to one silicon atom.

As used herein, the term "modification" or "surface modification" is intended to encompass both coating and doping, and, for example, may exist or be exposed in a form of discontinuous domains such as incorporation, dispersion, embedding, and island, or in a form of continuous domains, on the surface or outer portions of underlying materials (substrates) or matrixes.

As used herein, the term "heat treatment" or "thermal treatment" refers to an intentional temperature increase in the entirety or part of a subject, optionally with the entailment of additional chemical or physical treatment so as to achieve a desired specific structure and physical property (or change).

As used herein, the term "light paraffin" refers to a paraffin of 2 to 5 carbon atoms, more particularly, a paraffin of 3 or 4 carbon atoms, as exemplified by ethane, propane, n-butane, isobutane, and pentane. In addition, "corresponding olefin" refers to an olefin that results from the removal of a hydrogen molecule from a light paraffin in a feedstock through dehydrogenation and thus has the same number of carbon atoms as the paraffin.

Throughout the description, the terms "on" and "over" are used to refer to the relative positioning, and may mean not only that one component or layer is directly disposed on another component or layer but also that one component or layer is indirectly disposed on another component or layer, with a further component or layer (intermediate layer) interposed therebetween. Likewise, spatially relative terms such as "below", "beneath", "lower", and "between" may be used herein for ease of description to refer to the relative positioning. Also, the term "sequentially" may be understood to pertain to a relative positioning concept.

Throughout the description, unless explicitly described to the contrary, the word "comprise" and variations such as "comprises" or "comprising" will be understood to imply the inclusion of stated elements and/or steps, but not the exclusion of any other elements.

Dehydrogenation Catalyst and Method for Producing Same

An embodiment of the present disclosure provides a cobalt-based catalyst, particularly a heterogeneous catalyst comprising a single-atom cobalt as an active metal loaded onto a silica-modified zirconia support, that is suitable for a dehydrogenation reaction for converting a feedstock containing paraffins (particularly, light paraffins) to the corresponding olefins with a high conversion and high selectivity, provides excellent conversion of feedstock having a high paraffin content and exhibits improved long-term reaction stability or regenerability.

A. Preparation of Silica-Modified Zirconia Support

According to one embodiment, first, zirconia ($ZrO_2$) may be provided as an underlying or base material or as a core constituting the support. In this regard, zirconia may be selected from the types or species known in the art, or may be synthesized by a method known in the art (e.g., a liquid-phase reaction such as fast precipitation, sol-gel, solvent evaporation and hydrothermal treatment, or a vapor-phase reaction such as chemical vapor synthesis), for example, by hydrolyzing a zirconia precursor (e.g., zirconium (IV) n-pentoxide) in an alcohol solvent. In addition, zirconia may exhibit crystallinity, and may be classified into a monoclinic structure (m-$ZrO_2$), a tetragonal structure (t-$ZrO_2$), a cubic structure (c-$ZrO_2$), and the like. In this embodiment, zirconia, which is known in the art or is commercially available, may be used without particular limitation.

In this regard, the mechanical properties of zirconia and silica may be exemplified as shown in Table 1 below (AZO Materials, https://www.azom.com).

TABLE 1

| Item | Zirconia | | Silica | |
|---|---|---|---|---|
| | Minimum | Maximum | Minimum | Maximum |
| Shear modulus (GPa) | 53.4 | 86.4 | 27.9 | 32.3 |
| Tensile strength (MPa) | 115 | 711 | 45 | 155 |
| Young's modulus (GPa) | 100 | 250 | 66.3 | 74.8 |

As can be seen from the table above, zirconia may have better mechanical properties than silica. Accordingly, zirconia is capable of suppressing a decrease in strength even under high temperature environment as involved in a dehydrogenation of paraffin as described later, of stably maintaining catalytic activity even upon repeated reaction cycles, and of contributing to suppressing aggregation of cobalt single atom. Furthermore, zirconia is capable of changing the electronic properties of the loaded single-atom cobalt active sites and is thus advantageous in the dehydrogenation reaction.

In an exemplary embodiment, the zirconia used in the support has, for example, a BET specific surface area ranging from about 10 to about 300 $m^2/g$, particularly from about 20 to about 150 $m^2/g$, and more particularly from about 30 to about 100 $m^2/g$, and, for example, a pore size ranging from about 5 to about 40 nm, particularly from about 10 to 30 nm, and more particularly from about 15 to about 25 nm. Further, the zirconia may have, for example, a pore volume ranging from about 0.1 to about 1 $cm^3/g$, particularly from about 0.2 to about 0.5 $cm^3/g$, and more particularly from about 0.25 to about 0.3 $cm^3/g$. It may be advantageous to control these specifications of zirconia within the range described above because the morphology of zirconia acts as a factor affecting the content and thermal stability of single cobalt atoms, but the present disclosure is not limited thereto.

According to one embodiment, after providing zirconia as a core, the surface of the zirconia is modified with silica. In this case, the surface modification with silica may be performed based on a known method using a silica precursor. For example, the method includes an impregnation method (particularly, incipient wetness impregnation), a sol-gel method, or the like.

The method of surface-modifying zirconia with silica may be exemplified as follows, but the present disclosure is not necessarily limited thereto.

First, a silica precursor (or a silica source) may be dissolved in an aqueous medium to prepare an aqueous silica precursor solution. In this case, the aqueous medium may be water, particularly distilled water. In addition, the concentration of the silica precursor solution is, for example, adjusted to about 5 to 80% (w/w), particularly about 10 to 70% (w/w), and more particularly about 15 to 60% (w/w).

According to an exemplary embodiment, the silica precursor may be a low-cost precursor or compound such as soluble silicate, for example a silicate of an alkali metal, particularly sodium silicate (or water glass) or potassium silicate. Alternatively, the silica precursor may be alkoxysilane represented by $Si(OR)_4$, for example, tetramethoxysilane, tetraethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, butyltrimethoxysilane, isobutyltriethoxysilane, hexyltriethoxysilane, octyltriethoxysilane, or the like.

Then, the aqueous silica precursor solution may be combined with zirconia to prepare an aqueous dispersion. According to an exemplary embodiment, when the aqueous silica precursor solution is combined with the zirconia, the weight ratio of the silica precursor to zirconia is, for example, adjusted to 1: about 0.1 to 50, particularly 1: about 1 to 35, more particularly 1: about 3 to 25. In this case, the temperature at which the aqueous silica precursor solution contacts the zirconia is not particularly limited, but may be, for example, about 10 to 80° C., particularly about 15 to 50° C., and more particularly room temperature. In addition, the combination or contact may typically be performed for about 0.5 to 5 hours, more typically about 1 to about 2 hours, and may also be performed with or without stirring. Through this process, zirconia on which a silica precursor is loaded may be formed.

According to an exemplary embodiment, the silica precursor-loaded zirconia can be obtained from the silica precursor-loaded zirconia dispersion through conventional post-treatment, such as separation (e.g., filtration, standing, etc.) and/or purification, particularly removal of the silica precursor solution, washing (particularly, washing with water) and/or drying (e.g., drying under an inert gas (e.g., nitrogen atmosphere)).

Then, the silica precursor-loaded zirconia may be heat-treated to convert the loaded silica precursor into its oxide form, that is, silica, and as a result, silica-modified zirconia may be prepared as a support. Illustratively, the heat treatment or thermal treatment is performed at a temperature of about 500 to 1,200° C., particularly about 600 to 1,100° C., more particularly about 700 to 1,000° C., for example, about 1 to 12 hours, particularly about 2 to 9 hours, more particularly, about 3 to 5 hours. At this time, the heat treatment may be performed in an oxygen-containing atmosphere, for example, an air atmosphere, and the heating rate is, for example, controlled within from about 0.1 to 30° C./min, particularly from about 1 to 20° C./min, more particularly from about 2 to 10° C./min.

In this regard, the amount of silica in the silica-modified zirconia support is, for example, from about 0.5 to about 10% by weight, particularly from about 1 to about 6% by weight, more particularly from about 1.5 to about 4% by weight, particularly from about 2 to about 3.5% by weight. At this time, when the amount of silica is excessively small, the selectivity for olefin (e.g., propylene) may be deteriorated, whereas when the amount of silica is excessively great, the paraffin (e.g., propane) conversion may decrease. Thus, it is preferable that the amount of silica should be suitably adjusted within the range described above. However, these numerical ranges may be understood to be provided for illustration.

Meanwhile, silica may be present in various forms on the surface or outer portion of the zirconia core in the silica-modified zirconia support. However, it may be preferable that at least a part of silica is exposed to the outside in order to support the single-atom cobalt, which is a subsequent process. In an exemplary embodiment, the silica may be formed in the form of a discontinuous domain (e.g., in the form of an island), as shown in FIG. 1. In this case, the size of the silica domain may be controlled, for example, within the range of less than about 50 nm, particularly less than about 20 nm, and more particularly less than about 10 nm. The size of the silica domain may be changed depending on the amount of silica loaded on the zirconia core. When the amount of silica that is loaded exceeds a certain level, the domain size also increases (for example, to about 20 nm or more), thus having an undesirable effect on improvement in conversion and/or selectivity during dehydrogenation (particularly, dehydrogenation of propane).

Further, according to an exemplary embodiment, silica-modified zirconia has a higher specific surface area when subjected to heat treatment (e.g., at least about 30%, particularly at least about 40%, more particularly at least about 40%, more particularly, at least one 50%, compared to unmodified zirconia), which is considered to result from the increased thermal stability of zirconia due to the introduction of silica.

B. Loading of Single-Atom Cobalt

According to an embodiment of the present disclosure, the silica-modified zirconia may be used as a support for the single-atom cobalt-based catalyst. In this regard, the negatively charged SiO⁻ and a cobalt ion having an oxidation number of 2+ present on the exposed surface of silica (e.g., silica domain) on the zirconia core through surface modification of zirconia with silica may be bound to an isolated form of single-atom by electrostatic interaction or adsorption. Without being bound by a particular theory, the reason for this is considered to be that, as shown in Table 2 below, the zirconia support also has an isoelectric point of about 4, which is higher than the isoelectric point of silica (i.e., about 2), but is lower than that of other metal oxides, and thus it is advantageous to support cobalt under basic conditions. In addition, the cobalt single-atom active point generated on the support is considered to be more stable because the thermomechanical stability of zirconia is better than that of silica.

TABLE 2

| Metal oxide | Isoelectric Point |
|---|---|
| Silica | 2 |
| Zirconia | 4 |
| Titania (Anatase) | 3.5 |
| Titania (Rutile) | 6.5 |
| Alumina | 8 to 9 |

In addition, in this embodiment, by using zirconia as a core, it is possible to effectively induce cobalt to be loaded in a single-atom form by the silica domain having an appropriate morphology and size, and to stably maintain cobalt in a single-atom form without being aggregated or agglomerated due to the excellent thermal stability of the support.

In this case, the single-atom cobalt is coordinated to form a tetrahedral structure at a three-membered hydroxyl ring by three hydroxyl groups (trihydroxyl groups) present on the surface of silica in the support. This single-atom cobalt support may be performed as follows.

An aqueous dispersion of the silica-modified zirconia support described above is prepared. The aqueous medium used herein to prepare the dispersion may be water, particularly distilled water, and the amount of the silica-modified zirconia support in the aqueous dispersion is, for example, about 1 to 30% by weight, particularly about 3 to 20% by weight, and more particularly about 5 to 10% by weight.

Meanwhile, a base is added to the aqueous dispersion of the silica-modified zirconia support to prepare the pH-adjusted silica-modified zirconia dispersion, and the pH of the aqueous dispersion of silica-modified zirconia is, for example, adjusted within the range of at least about 10, particularly at least about 11, more particularly, from about 10.5 to about 11.5. The reason for increasing the pH of the dispersion is to deprotonate the surface of the exposed silica on the zirconia. Specifically, hydrogen ions may be removed from the hydroxyl groups present on the surface of the silica to thereby impart a negative charge to the silica. That is, since ions are not adsorbed at the point of zero charge of silica and the hydroxyl groups are maintained, the silica surface is negatively charged by deprotonation through pH adjustment. As a result, three hydroxyl groups, present on the silica surface, form three deprotonated hydroxyl groups in a basic aqueous medium, providing sites to which cobalt is immobilized (fixed) in the form of a single atom in the subsequent step.

According to an exemplary embodiment, the base may be, for example, an aqueous solution of sodium hydroxide, potassium hydroxide, ammonium hydroxide, or the like, particularly an ammonium-containing base, more particularly ammonium hydroxide (ammonia water). The base to be added is preferably a type of base that does not cause precipitation when combined or mixed with an aqueous solution of a cobalt precursor.

Meanwhile, according to one embodiment of the present disclosure, separately from the step of preparing the pH-adjusted aqueous dispersion of the silica-modified zirconia described above, a step of preparing an aqueous solution of a cobalt precursor and then adding a base thereto may be performed to prepare a pH-adjusted aqueous cobalt precursor solution.

In this regard, the cobalt precursor may be a precursor including a cobalt (Co(III)) complex ion having an oxidation value of 3+. For example, $Co(NH_3)_6Cl_3$ may be used directly, or at least one cobalt compound (precursor) selected from $Co(NO_3)_2$, $CoCl_2$, $Co(acac)_3$, and the like may be treated with ammonia water and then filtered to obtain a precursor containing a cobalt complex ion. The employment of $Co(NH_3)_6Cl_3$ may be advantageous for easygoing formation of a cobalt single-atom catalyst because it can minimize the preparation steps.

In an exemplary embodiment, the concentration of the cobalt precursor in the aqueous precursor solution may range, for example, from about 0.1% to about 20% by weight, particularly from about 0.5% to about 10% by weight, and more particularly from about 1% to about 5% by weight.

In addition, the pH of the cobalt precursor solution can be adjusted through addition of a base. The pH adjustment enables the exposed silica surface of the support to stably retain a deprotonated state (that is, modified to have a negative charge) upon combination with the aqueous dispersion of the pH-adjusted silica-modified zirconia in the subsequent step, whereby the positively charged cobalt ions ($Co^{3+}$) of the precursor can be fixed or attached to the silica surface of the silica-modified zirconia support through electrostatic adsorption.

In this case, the base may be at least one selected from those used for the preparation of the aqueous dispersion. By way of example, the base or basic compounds used in each of the preparation steps may be the same. According to circumstances, different base may be employed. Even in this case, the base that does not cause precipitation when mixed with an aqueous solution of the cobalt precursor is desirable. In an exemplary embodiment, the addition of a base can adjust the pH of the aqueous cobalt precursor solution to, for example, at least about 10, particularly at least about 11, and more particularly about 10.5 to 11.5.

Once the pH-adjusted aqueous solution of the Co(III) precursor is prepared, the combination with the pH-adjusted aqueous dispersion of the silica-modified zirconia is performed. The mixing ratio of the pH-adjusted aqueous cobalt precursor solution to the pH-adjusted aqueous silica-modified zirconia dispersion may be determined depending on the amount of cobalt ions in the aqueous cobalt precursor solution, which is to be fixed in the form of a single atom (particularly, a single-atom of a single layer) on the silica surface of the silica-modified zirconia support.

In this regard, cobalt ions can be loaded in an amount of about 0.1% to about 2% by weight, particularly about 0.15% to 1% by weight, more particularly about 0.2% to 0.4% by weight, on the silica surface of the silica-modified zirconia support. However, all of the cobalt precursor used cannot be fixed onto the surface of the silica-modified zirconia support in practice. Thus, an excess of a cobalt (Co(III)) precursor larger than the theoretical amount may be dissolved therein. In an exemplary embodiment, the mixing ratio of the aqueous solution of cobalt precursor to the aqueous dispersion of silica-modified zirconia may be adjusted so that the amount of the cobalt precursor falls within the range of about 0.1% to about 10% by weight, particularly about 0.5% to about 8% by weight, more particularly about 1% to about 6% by weight, based on the weight of the silica-modified zirconia.

According to an exemplary embodiment, the combination of the two aqueous fluids (i.e., the aqueous silica-modified zirconia dispersion and the aqueous cobalt precursor solution) may be performed with stirring. Here, the stirring speed may be in the range of, for example, about 200 to 500 rpm, particularly about 250 to 400 rpm, and the stirring time is, for example, at least about 3 minutes, particularly at least about 5 minutes, and more particularly about 5 to 10 minutes, but the present disclosure is not limited to the above ranges. In addition, the mixing temperature is not particularly limited, and may be, for example, about 10 to about 40° C., particularly about 20 to about 30° C., and more particularly room temperature.

Then, cobalt ions not adsorbed on the surface of the silica-modified zirconia support are removed as completely as possible. This is different from the conventional impregnation and aims to leave only cobalt (or $Co^{3+}$) fixed to the silica surface in a single-atom form through electrical interaction while eliminating the others. For example, when the cobalt precursor is attached in a bulk state onto a silica surface, as in the conventional impregnation, induces reduction, aggregation, etc., which lowers catalytic activity during the dehydrogenation reaction.

In exemplary embodiments, the solids (silica-modified zirconia support on which the cobalt precursor is adsorbed (fixed)) in the combined dispersion can be separated through any conventional solid-liquid separation process such as settling or filtering. As necessary, the separated solids may be subjected to repeated cycles of adding water, particularly distilled water, stirring, and separating.

Furthermore, the separated solids may be washed at least once, particularly, two or more times with water, particularly distilled water, to remove as much the cobalt precursor remaining unattached as possible. Next, the solids thus obtained may be dried at a temperature of, for example, about 10 to 40° C., particularly about 20 to 30° C., and more particularly at room temperature, but without limitation thereto. At this time, the cobalt ions still retain an oxidation number of +3.

In a subsequent step, the silica-modified zirconia support on which the cobalt ions are adsorbed (immobilized) is converted to a dehydrogenation catalyst through thermal treatment. This thermal treatment may be performed under an oxygen-containing atmosphere; for example, the thermal treatment temperature may be set within the range of about 250 to 1,000° C., particularly about 275 to 800° C., and more particularly about 300 to 600° C. In this embodiment, as the cobalt-adsorbed (fixed) silica-modified zirconia support is thermally treated, the cobalt adsorbed onto the silica changes in oxidation number from 3+ to 2+. In addition, the temperature elevation rate in the thermal treatment is, for example, controlled within the range of about 0.1 to 20° C./min, particularly, about 1 to 10° C./min, and more particularly, about 2 to 5° C./min.

Optionally, an additional drying step may be performed prior to the thermal treatment under an oxygen-containing atmosphere. In this case, the temperature in the additional drying step may be, for example, in the range of about 50 to 150° C., particularly about 120 to 150° C. In this relatively high-temperature drying process, at least a part of cobalt atoms having an oxidation number of 3+ may be partially reduced to cobalt atoms having an oxidation number of 2+ in advance.

Without being bound by a particular theory, the reason why the cobalt retains an oxidation number of 2+ after the thermal treatment is explained as follows.

For cobalt having an oxidation number of 3+, only the octahedral structure is possible because six electrons occupy the outmost orbital to enable the formation of six bonds. When the oxidation number of cobalt is reduced to 2+, seven electrons exist in the outmost orbital, thus mainly forming a tetrahedral structure, while an octahedral structure is also possible as in CoO. According to the present embodiment, it is supposed that the cobalt is reduced to 2+ to form a tetrahedral structure because it should structurally bind to the three-membered hydroxyl groups (or trihydroxyl groups). On the other hand, in order to return back to 3+, the cobalt should form an octahedron in cooperation with its surroundings. At this time, silicon (Si) does not have any structure other than a tetrahedron in nature, which is in discord with the octahedral structure of cobalt, and thus making it difficult to convert the reduced cobalt to the oxidized state 3+. Moreover, the deactivation arises when the linkage (communication) to Si is cleaved to cause Co metal to aggregate alone. Accordingly, it is considered that the formation of an oxide by contact with oxygen could result in $Co_3O_4$ containing cobalt of the oxidation state 3+.

In addition, so long as it guarantees the conversion of the oxidation number of cobalt from 3+ to 2+, any time could be set for the heat treatment and may be, for example, about 2 to 12 hours, particularly about 2.5 to 8 hours, and more particularly about 3 to 4 hours, but are not particularly limited thereto.

The cobalt with the oxidation number 2+, converted by heating at a predetermined temperature or higher during the thermal treatment, is not returned back to the oxidation number 3+ even though the thermal treatment is continued in an oxygen-containing (or oxidation) atmosphere (or calcining atmosphere). The reason is because the single-atom cobalt needs to retain a tetrahedral structure. Furthermore, even when the catalyst is applied to the dehydrogenation conducted at a predetermined temperature or higher, the oxidation state remains unchanged, implying that the catalyst according to the present embodiment is resistant to reduction. In particular, the cobalt single-atom catalyst according to one embodiment provides advantageous properties in terms of long-term reaction stability or regeneration stability during the dehydrogenation reaction by forming the underlying structure of silica (particularly, silica domains) with zirconia.

Without being bound by a particular theory, the cobalt in the catalyst maintains a single-atom form, but as the electronic properties of the cobalt active sites change due to the presence of underlying zirconia, the activity, selectivity and/or stability are controlled to favor the dehydrogenation reaction. That is, when only zirconia is used as a support, the electron density of single cobalt atoms is low, so the reactant/product is strongly adsorbed to cobalt. As a result, the conversion of propane increases, but the selectivity for propylene decreases while coke formation increases. In contrast, the electron density of the cobalt single atom, formed as a result of the combination of silica with the zirconia core, increases, and the reactant/product is relatively weakly adsorbed to the cobalt, so propane conversion decreases while propylene selectivity increases, and coke formation is also suppressed.

According to an exemplary embodiment, the content of cobalt (loading amount of cobalt) in the dehydrogenation catalyst is, for example, about 0.05 to about 2% by weight, particularly about 0.1 to about 1.5% by weight, more particularly about 0.15 to about 1% by weight, and even more particularly about 0.2 to about 0.4% by weight.

Dehydrogenation

According to another embodiment of the present disclosure, paraffin, particularly light paraffin (more particularly, light paraffin having 2 to 5 carbon atoms) is converted to the corresponding olefin through dehydrogenation using the cobalt-based catalyst in the form of single-atom, as described above. In particular, the light paraffin may include propane. In this regard, the feedstock may be provided in a gas phase.

Notably, when applied even to a feedstock containing a high content of paraffins, the catalyst can achieve better conversion and selectivity. By way of example, the content of paraffins in a feedstock may be, for example, at least about 50% by volume, particularly at least about 70% by volume, more particularly at least about 80% by volume, and higher than about 99% by volume. This differs from the experimental results in which a feedstock containing paraffins at most about 20% by volume is subjected to dehydrogenation in the presence of the conventional single-atom catalyst (e.g., Zn catalyst).

In the dehydrogenation according to an exemplary embodiment, the reaction temperature may range, for example, from about 500 to 700° C., particularly from about 550 to 650° C., and more particularly from about 570 to 620° C. In addition, a pressure of, for example, about 0.3 to 2 bar, particularly about 0.4 to 1.5 bar, and more particularly about 0.5 to 1 bar may be set for the dehydrogenation. As for the gas hourly space velocity (GHSV), its range may be chosen to be, for example, about 100 to 2000 $hr^{-1}$, particularly about 200 to 1500 $hr^{-1}$, and more particularly about 300 to 1000 $hr^{-1}$ in a standard condition. The dehydrogenation conditions may vary depending on kinds of paraffins in the feedstock, the loading amount of active metal (cobalt) in the catalyst, etc.

According to an exemplary embodiment, each of the conversion and selectivity in the dehydrogenation process is, for example, at least about 30% (particularly at least about 40%, more particularly at least about 45%), and at least about 70% (particularly at least about 80%, particularly at least about 85%).

The present disclosure will be further clearly understood with reference to the following examples. However, the following examples are provided only for illustration of the present disclosure, and thus should not be construed as limiting the scope of the present disclosure.

EXAMPLE

Conversion and selectivity of propane in this example were calculated according to Equations 1 and 2 below.

$$\text{Conversion Rate of propane (\%)} = \frac{\text{Weight of propane in reactant} - \text{Weight of unconverted propane in product}}{\text{Weight of propane in reactant}} \times 100 \quad [\text{Equation 1}]$$

$$\text{Selectivity for propylene (\%)} = \frac{\text{Weight of propylene in product}}{\text{Weight of propane in reactant} - \text{Weight of unconverted propane in product}} \quad [\text{Equation 2}]$$

Preparation Example 1

First, five batches were separately prepared using 10 g of commercially available zirconia (5Z31164 produced by Saint-Gobain; specific surface area: 85 $m^2/g$, pore volume: 0.29 $cm^3/g$, pore size: 8.60 nm) (zirconia particle size: 16-40 mesh; volume: 6 cc) as a core.

Separately, 0.483 g, 0.966 g, 1.449 g, 1.932 g, and 2.898 g of $Na_2SiO_3.9H_2O$ were dissolved in 4 ml of distilled water in beakers such that the content of silica incorporated into the prepared zirconia was 1% by weight, 2% by weight, 3% by weight, 4% by weight and 6% by weight, respectively, to prepare aqueous silica precursor solutions.

Next, each of the aqueous silica precursor solutions was added to 10 g of the previously prepared zirconia and mixed for 1 hour using a roll mixer. Then, the aqueous silica precursor solution was dried in an oven at 80° C. to obtain silica precursor-loaded zirconia.

The silica precursor-loaded zirconia thus obtained was heated to 750° C. at a temperature elevation rate of 5° C./min and then thermally treated in air for 3 hours to prepare 1% by weight, 2% by weight, 3% by weight, 4% by weight and 6% by weight of silica-modified zirconia supports. These silica-modified zirconia supports were designated as "1Si@Zr", "2Si@Zr", "3Si@Zr", "4Si@Zr", and "6Si@Zr" depending on the silica content, respectively.

Preparation Example 2

10 g of each of xSi@Zr (x=1, 2, 3, 4, 6) supports prepared in Preparation Example 1 was dispersed in 100 ml of distilled water and was added with 28% by weight of concentrated ammonia water (Samjeon Chemical Co., Ltd.) to prepare a pH-adjusted xSi@Zr (x=1, 2, 3, 4, 6) aqueous dispersion having a pH of 11.

Separately, 0.5 g of a cobalt precursor ($Co(NR_3)_6Cl_3$) was dissolved in 50 ml of distilled water in a beaker, and was added with 28% by weight of concentrated ammonia water (Samjeon Chemical Co., Ltd.) to prepare a pH-adjusted aqueous precursor solution having a pH of 11.

Next, the pH-adjusted, aqueous cobalt precursor solution was quickly added to the pH-adjusted aqueous dispersion of xSi@Zr and stirred at room temperature for 30 minutes. The stirred sample was allowed to stand for 5 minutes, the liquid phase was discarded, 200 ml of distilled water was poured over the residue again, the resulting mixture was stirred for 10 minutes, and the sample was filtered under reduced pressure and washed several times with distilled water.

The filtered sample was dried at room temperature and then dried again at 125° C. The dried sample was heated to 300° C. at a temperature elevation rate of 5° C./min and then thermally treated in air for 3 hours to prepare dehydrogenation catalysts (Co/1Si@Zr, Co/2Si@Zr, Co/3Si@Zr, Co/4Si@Zr, and Co/6Si@Zr catalysts).

Comparative Preparation Example 1

10 g of commercially available zirconia (SZ31164 from Saint-Gobain; specific surface area: 85 m²/g, pore volume: 0.29 cm³/g, pore size: 8.60 nm) (zirconia particle size: 16 to 40 mesh; volume 6 cc) was dispersed in 100 ml of distilled water and was added with 28% by weight of concentrated ammonia water (Samjeon Chemical Co., Ltd.) to prepare a pH-adjusted aqueous zirconia dispersion having a pH of 11.

Separately, 0.5 g of a cobalt precursor (($Co(NH_3)_6Cl_3$) was dissolved in 50 ml of distilled water in a beaker, and was added with 28% by weight of concentrated ammonia water (Samjeon Chemical Co., Ltd.) to prepare a pH-adjusted aqueous cobalt precursor solution having a pH of 11.

Next, the pH-adjusted, aqueous cobalt precursor solution was rapidly added to the pH-adjusted aqueous zirconia dispersion and stirred at room temperature for 30 minutes. The stirred sample was allowed to stand for 5 minutes, the liquid phase was discarded off, 200 ml of distilled water was poured over the residue again, the resulting mixture was stirred for 10 minutes, and the sample was filtered under reduced pressure and washed several times with distilled water.

The filtered sample was dried at room temperature and then dried again at 125° C. The dried sample was heated to 300° C. at a temperature elevation rate of 5° C./min and then thermally treated in air for 3 hours to prepare a dehydrogenation catalyst (Co/Zr catalyst).

The silica content and cobalt content of the catalysts (Co/Zr, Co/1Si@Zr, Co/2Si@Zr, Co/3Si@Zr, Co/4Si@Zr, and Co/6Si@Zr) prepared according to Preparation Example 2 and Comparative Preparation Example 1 were analyzed using inductively coupled plasma optical analysis (ICP-OES), and the results are shown in Table 3 below.

TABLE 3

| Catalyst | SiO₂ content (wt %) | Co content (wt %) |
|---|---|---|
| Co/Zr | 0 | 0.2 |
| Co/1Si@Zr | 0.8 | 0.2 |
| Co/2Si@Zr | 1.5 | 0.2 |
| Co/3Si@Zr | 2.8 | 0.2 |
| Co/4Si@Zr | 3.9 | 0.2 |
| Co/6Si@Zr | 5.6 | 0.2 |

Experimental Example 1

Figure 2:
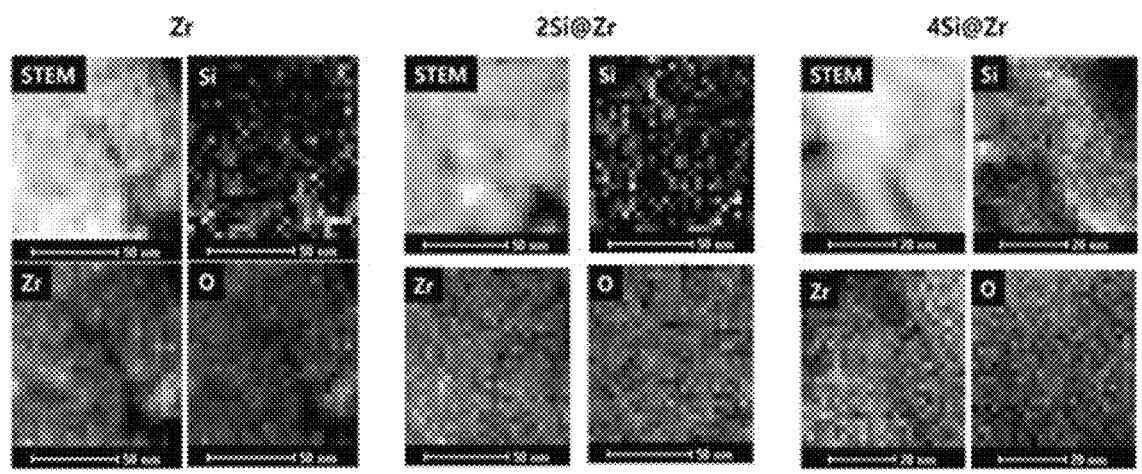
FIG. 2 is a scanning transmission electron microscope energy dispersive spectroscopy (STEM-EDS) image of an xSi@Zr catalyst prepared while changing the content of silica used to surface-modify the zirconia core (particle size: 16 to 40 mesh; volume: 6 cc) to 0% by weight, 2% by weight, and 4% by weight.

In this experimental example, for the prepared Zr, 2Si@Zr, and 4Si@Zr, the domain size of silica was analyzed using scanning transmission electron microscope energy dispersive spectroscopy (STEM-EDS), and the results are shown in FIG. 2.

As can be seen from FIG. 2, when silica was introduced in an amount of 4% by weight or more, silica domains having a size in the range of 20 to 50 nm were observed. On the other hand, when silica was introduced in an amount lower than 4% by weight, silica domains having a size in the range of 20 to 50 nm could not be observed by STEM-EDS, which means that the size of the silica domains was less than 20 nm.

Experimental Example 2

In this experimental example, the change in specific surface area resulting from the introduction of silica onto zirconia and thermal treatment was analyzed, and the results are shown in Table 4. Analysis was performed using Micromeritics 3felx, and all samples were degassed at 573 K for 12 hours before analysis. Nitrogen adsorption-desorption isotherms were measured at the temperature of liquid nitrogen (77 K). The result of the measurement showed that the silica-modified zirconia had a higher specific surface area after thermal treatment at 1023K compared to the non-silica-modified zirconia.

TABLE 4

| Catalyst (after heat treatment at 1023K) | BET specific surface area (m²/g) |
|---|---|
| Zr (before heat treatment) | 85 |
| Zr | 32 |
| 1Si@Zr | 45 |
| 2Si@Zr | 50 |
| 3Si@Zr | 48 |
| 4Si@Zr | 35 |
| 6Si@Zr | 36 |

Experimental Example 3

Figure 3:
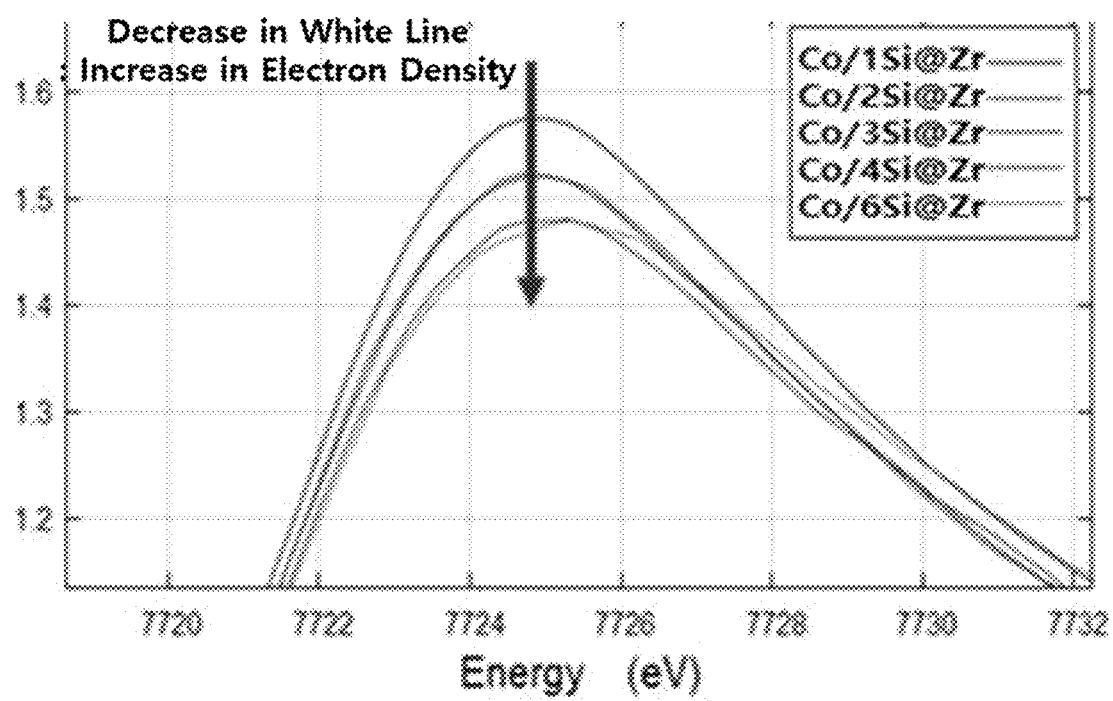
FIG. 3 is a graph illustrating an intensity of a white line of cobalt K-edge XANES for a cobalt single-atom catalyst prepared while changing the amount of silica used to surface-modify the zirconia core (particle size: 16 to 40 mesh; volume: 6 cc) from 1% by weight to 6% by weight.

In this experimental example, the intensity of a white line of a Co K-edge XANES spectrum with respect to Co/xSi@Zr (x=1-6) prepared by introducing silica onto zirconia was compared to evaluate the electron density of a single cobalt atom, and the results are shown in FIG. 3. At this time, the analysis was performed at the 8C beamline of the Pohang light source (PLS) of Pohang Accelerator Laboratory (PAL).

As can be seen from FIG. 3, as the silica content increased, the intensity of a white line of cobalt K-edge XANES gradually decreased, and the electron density of single cobalt atoms increased.

Experimental Example 4

In this experimental example, a dehydrogenation reaction for synthesizing olefins from a reactant gas containing a high paraffin content was performed in the presence of the cobalt-based catalysts (Co/Zr, Co/1Si@Zr, Co/2Si@Zr, Co/3Si@Zr, Co/4Si@Zr, and Co/6Si@Zr).

The dehydrogenation reaction for catalyst evaluation was performed using a ¾ inch quartz tube reactor (the diameter of the catalyst loading area was ¾ inch, and the diameter of the tube, excluding the loading area, was ¼ inch). Each gas flow rate was controlled using a mass flow controller, and the product gas passing through the reactor was analyzed through an on-line gas chromatography apparatus (50 m HP-PLOT column).

6 cc of each catalyst was weighed and loaded by quartz wool in the reaction tube through which $N_2$ (99.999%, Daesung Industrial Gases Co., Ltd.) was then allowed to flow at a flow rate of 100 cc/min while the temperature was elevated from room temperature to 590° C. at a rate of 5° C./min. Then, the same temperature was maintained for 1 hour for stabilization.

Figure 4:
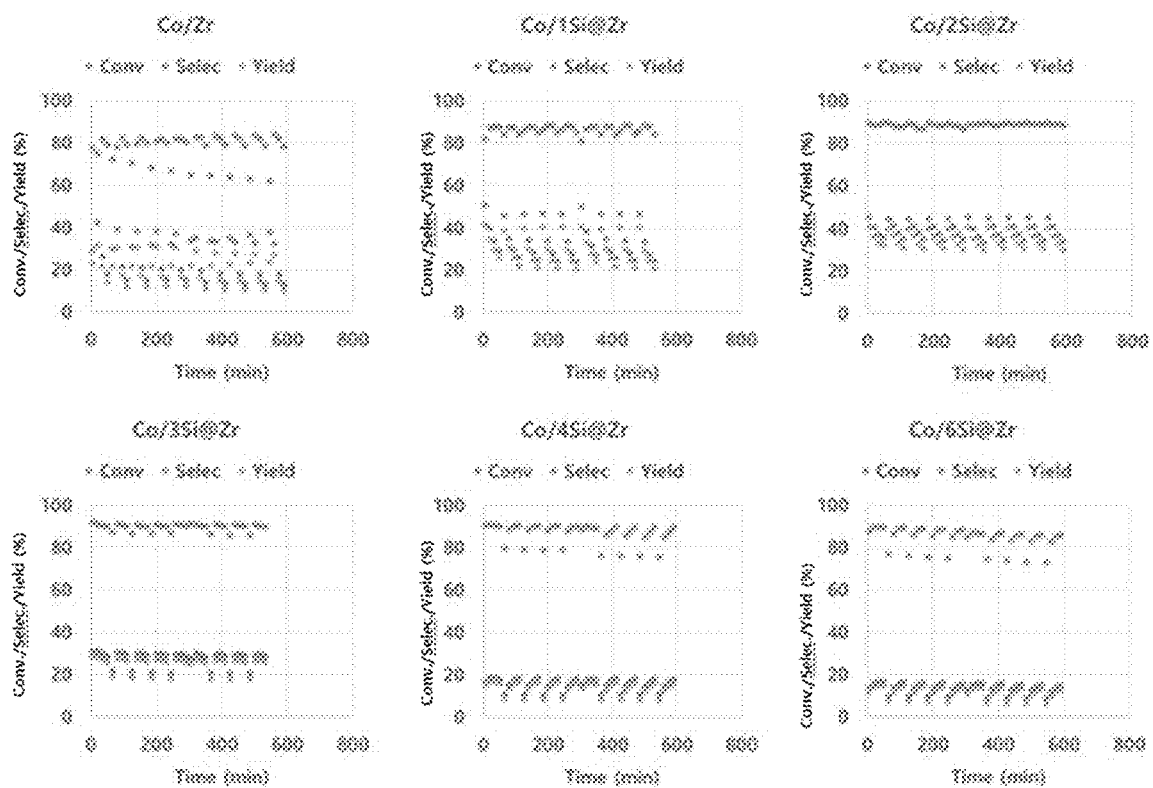
FIG. 4 is a graph illustrating the results of dehydrogenation (conversion, selectivity, and yield as a function of time) of propane in the presence of a cobalt single-atom catalyst prepared while changing the amount of silica used to surface-modify the zirconia core (particle size: 16 to 40 mesh; volume 6 cc) from 0% by weight to 6% by weight.

For the dehydrogenation reaction of paraffin, as the reactant gas, 99.5% propane (regas) was introduced at a flow rate of 20 cc/min, and $N_2$ (99.999%, Daesung Industrial Gases Co., Ltd.) was introduced at a flow rate of 30 cc/min, so the molar fraction of propane in the feedstock was 40%. The reaction was performed at 590° C. under atmospheric pressure, and the composition of the product gas passing through the reactor was analyzed using a flame ionization detector (FID) at 15-minute intervals. After the reaction proceeded for 1 hour, the catalyst was regenerated in an air atmosphere at the same temperature for 30 minutes, and $N_2$ (99.999%, Daesung Industrial Gases Co., Ltd.) was introduced for 15 minutes between the reaction and regeneration. The reaction results (conversion, selectivity and yield over time) are shown in FIG. 4. Here, four points per hour constitute one cycle. After four points were measured (for 1 hour), regeneration was performed, and the next four points were taken as the next cycle. Thus, the first one among the four points corresponds to the initial conversion/selectivity/yield.

Referring to FIG. 4, the result of the dehydrogenation showed that the cobalt-loaded catalyst (Co/Zr) prepared using the zirconia support not modified with silica exhibited a very high initial conversion of 80%, but low propylene selectivity of 30%. In addition, as regeneration proceeded, propylene selectivity decreased to about 60% and the initial conversion also decreased.

Meanwhile, when the content of silica in the silica-modified zirconia support was 2% by weight (Co/2Si@Zr), although the initial conversion was approximately 46%, the selectivity was 90%, and no decrease in initial conversion or selectivity was observed, despite the catalyst regeneration.

In addition, when the content of silica in the silica-modified zirconia support was 4% by weight (Co/4Si@Zr), selectivity was maintained, but conversion was gradually decreased, and when the silica content was 6% by weight, a further decrease in Co/6Si@Zr conversion was observed.

Experimental Example 5

In this experimental example, the propane dehydrogenation and catalyst regeneration experiments were performed 200 times in the presence of the Co/2Si@Zr catalyst, which exhibited the best results in Experimental Example 1. Like the commercial propane dehydrogenation process (Catofin), the reaction was performed for 15 minutes, the catalyst was regenerated in an air atmosphere at the same temperature for 15 minutes, and $N_2$ (99.999%, Daesung Industrial Gases Co., Ltd.) was introduced for 15 minutes between the reaction and regeneration. The results of 200 catalytic reaction-regeneration cycles are shown in FIG. 5.

Figure 5:
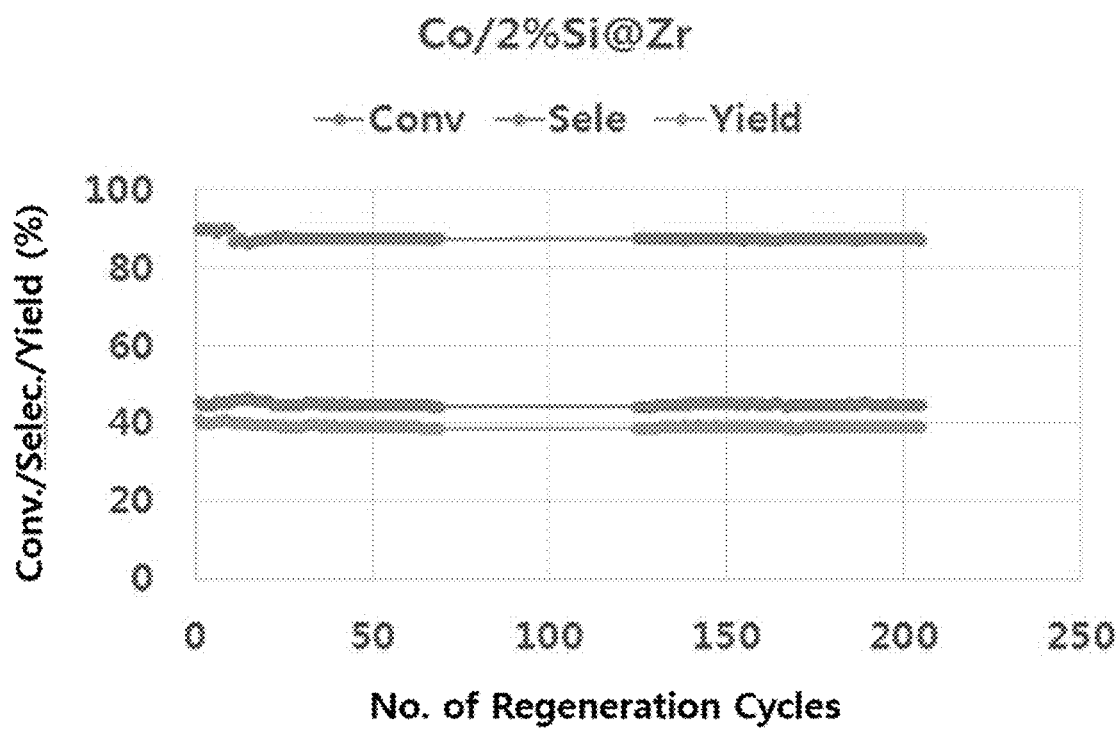
FIG. 5 is a graph illustrating the results of dehydrogenation (conversion, selectivity, and yield as a function of the number of reproduction cycles) of propane in the presence of a cobalt single-atom catalyst prepared using a silica-modified zirconia (particle size: 16 to 40 mesh; volume: 6 cc; silica content: 2% by weight) support.

As can be seen from FIG. 5, the conversion and selectivity were maintained constant regardless of the number of recycling cycles of the catalyst.

Accordingly, it should be understood that simple modifications and variations of the present disclosure may be easily used by those skilled in the art, and such modifications or variations may fall within the scope of the present disclosure.

What is claimed is:

1. A method for producing a single-atom cobalt catalyst, which comprises:
   a) surface-modifying a surface of zirconia with silica by use of silica precursor to prepare a silica-modified zirconia support,
   b) preparing an aqueous dispersion of the silica-modified zirconia support,
   c) preparing a pH-adjusted aqueous dispersion of the silica-modified zirconia support by adding a base to the aqueous dispersion of the silica-modified zirconia support to adjust a pH of the aqueous dispersion to at least 10,
   d) separately, preparing a pH-adjusted aqueous cobalt precursor solution by preparing an aqueous solution of a cobalt precursor having an oxidation number of 3+ and adding a base to the aqueous solution,
   e) combining the pH-adjusted aqueous dispersion of the silica-modified zirconia support with the pH-adjusted aqueous solution of the cobalt precursor to prepare an aqueous dispersion in which at least a part of the cobalt ions having an oxidation number of 3+ is adsorbed onto a surface of the silica-modified zirconia support,
   f) removing cobalt ions which remain not adsorbed onto the silica-modified zirconia support, and
   g) thermally treating the cobalt ion-adsorbed silica-modified zirconia support obtained in step f),
   wherein the single-atom cobalt catalyst comprises a silica-modified zirconia support, in which zirconia, as a core, has been surface-modified with silica, and cobalt loaded as an active metal on the silica-modified zirconia support, the silica-modified zirconia support having a structure in which at least a part of the silica is exposed on an outside surface of the zirconia, and
   wherein the cobalt having an oxidation number of 2+ exists in an isolated form of single-atom on the silica-modified zirconia support while being tetrahedrally coordinated at a three-membered hydroxyl ring on the surface of the silica-modified zirconia support, wherein the silica exposed on the outside surface of the silica-modified zirconia support has a discontinuous domain of island which has a size less than 50 nm.

2. The method according to claim 1, wherein the zirconia has a BET specific surface area ranging from 10 to 300 m²/g and a pore size ranging from 5 to 40 nm.

3. The method according to claim 2, wherein the zirconia has a pore volume ranging from 0.1 to 1 cm³/g.

4. The method according to claim 1, wherein the step a) is performed by impregnation.

5. The method according to claim 4, wherein the step a) comprises:
   a1) dissolving the silica precursor in an aqueous medium to prepare an aqueous silica precursor solution having a concentration of 5 to 80% (w/w);
   a2) combining the aqueous silica precursor solution with zirconia to prepare a silica precursor-loaded zirconia aqueous dispersion;
   a3) separating silica precursor-loaded zirconia from the silica precursor-loaded zirconia aqueous dispersion; and
   a4) thermally treating the silica precursor-loaded zirconia at 500 to 1,200° C. in an oxygen-containing atmosphere.

6. The method according to claim 1, wherein a content of silica in the silica-modified zirconia support is determined in the range of 0.5 to 10% by weight.

7. The method according to claim 1, wherein a concentration of the aqueous dispersion of the silica-modified zirconia support prepared in step b) is in a range of 1 to 30% by weight.

8. The method according to claim 1, wherein the base used in each of steps c) and d) is the same as or different from each other and is at least one selected from the group consisting of sodium hydroxide, potassium hydroxide, and ammonium hydroxide.

9. The method according to claim 1, wherein the cobalt precursor in step d) is a precursor containing a cobalt (Co(III)) complex ion having an oxidation value of 3+, and
   a concentration of the cobalt precursor in the aqueous solution of the cobalt precursor is in a range of 0.1 to 20% by weight.

10. The method according to claim 1, wherein the silica-modified zirconia support on which cobalt ions are adsorbed has a structure in which the cobalt ions are loaded in an amount of 0.1 to 2% by weight on a silica surface of the silica-modified zirconia support.

11. The method according to claim 9, wherein the cobalt precursor is $Co(NH_3)_6Cl_3$, or contains a cobalt complex ion obtained by treating at least one cobalt compound selected from the group consisting of $Co(NO_3)_2$, $CoCl_2$, and $Co(acac)_3$ with ammonia water, followed by filtration.

12. The method according to claim 1, wherein the thermally treating is performed in an oxygen-containing atmosphere at a temperature of 250 to 1,000° C.

* * * * *